United States Patent
Hamada et al.

(10) Patent No.: US 8,273,889 B2
(45) Date of Patent: Sep. 25, 2012

(54) METHOD FOR PRODUCING 2-AZAADAMANTANE

(75) Inventors: Toshimasa Hamada, Tokyo (JP); Noriaki Nagahama, Funabashi (JP); Masami Kozawa, Funabashi (JP); Yoshiharu Iwabuchi, Sendai (JP); Masatoshi Shibuya, Sendai (JP); Masaki Tomizawa, Sendai (JP); Yusuke Sasano, Sendai (JP)

(73) Assignees: Nissan Chemical Industries, Ltd., Tokyo (JP); Tohoku Techno Arch Co., Ltd., Sendai-shi (JP)

( * ) Notice: Subject to any disclaimer, the term of this patent is extended or adjusted under 35 U.S.C. 154(b) by 21 days.

(21) Appl. No.: 12/744,015

(22) PCT Filed: Nov. 20, 2008

(86) PCT No.: PCT/JP2008/071143
§ 371 (c)(1),
(2), (4) Date: May 20, 2010

(87) PCT Pub. No.: WO2009/066735
PCT Pub. Date: May 28, 2009

(65) Prior Publication Data
US 2010/0311977 A1 Dec. 9, 2010

(30) Foreign Application Priority Data
Nov. 20, 2007 (JP) .................. 2007-300919

(51) Int. Cl.
*C07D 451/14* (2006.01)
*C07C 61/29* (2006.01)
*C07C 211/41* (2006.01)
*C07C 247/00* (2006.01)
*C07C 271/24* (2006.01)

(52) U.S. Cl. .............. 546/94; 552/5; 560/115; 562/500; 564/460

(58) Field of Classification Search ........................ None
See application file for complete search history.

(56) References Cited

FOREIGN PATENT DOCUMENTS

| EP | 1 775 296 A1 | 4/2007 |
|---|---|---|
| WO | 2006 001387 | 1/2006 |
| WO | WO 2009/145323 A1 | 12/2009 |

OTHER PUBLICATIONS

F. Zaragoza Dorwald, Side Reactions in Organic Synthesis; A Guide to Successful Synthesis Design, WILEY-VCH, Weinheim, Preface, p. IX (2005).*

Acidity Tables for Heteroatom Organic Acids and Carbon Acids [online Nov. 19, 2007] [retrieved on Oct. 28, 2011]. Retrieved from the Internet: <URL: http://renaud.dcb.unibe.ch/renaud_hp/OC1_files/pKa_org.pdf>.*

Sasaki, T. et al., "Synthesis and Acidolysis of 3-endo-Azidomethyl- and 3-endo-Azido-bicyclo [3.3.1]non-6-enes. A Novel Synthesis of 4-Azahomoadamant-4-enes", Journal of the Chemical Society, Perkin Transactions, vol. 1, No. 10, pp. 2529-2534, (1983).

Staas, H. Williams et al., Synthesis and Reactions of 4-Sunstituted 2-Azaadamantanes, Journal of Organic Chemistry, vol. 39, No. 26, pp. 3822-3827, (1974).

Lessard, Jean et al., "Chromous Chloride Promoted Cyclization of Olefinic N-Chloro Amides. Synthesis of Nitrogen Heterocycles", Journal of Organic Chemistry, vol. 43, No. 19, pp. 3750-3756, (1978).

Shibuya, Masatoshi et al., "2-Azaadamantane N-Oxyl (AZADO) and 1-Me-AZADO: Highly Efficient Organocatalysts for Oxidation of Alcohols", J. Am. Chem. Soc., vol. 128, No. 26, pp. 8412-8413, (2006).

Henkel, G. James et al., "Neighboring Group Effects in the β-Halo Amines. Synthesis and Solvolytic Reactivity of the anti-4-Substituted 2-Azaadamantyl System", J. Org. Chem., vol. 46, No. 24, pp. 4953-4959, (1981).

Henkel, G. James et al., "A General Synthesis of N-Substituted 2-Azaadamantanes and Their 4,8-Disubstituted Derivatives", J. Org. Chem., vol. 46, No. 17, pp. 3483-3486, (1981).

Stetter H. et al., Ringschlussreaktionen auf der Basis von cis, cis-1,5-Cyclo-octadien [2]), Chem. Ber., vol. 106, pp. 339-348, (1973).

Stetter H. et al., Ringschlussreaktionen ausgehend von Bicyclo[3.3.1]nonandion-(3.7), Chem, Ber., vol. 97, pp. 3480-3487, (1964).

Extended European Search Report issued Nov. 26, 2010 in PCT/JP2008071143.

Alan P. Kozikowski, et al., "An Approach to Open Chain and Modified Heterocyclic Analogues of the Acetylcholinesterase Inhibitor, Huperzine A, Through a Bicyclo[3.3.1]Nonane Intermediate", Heterocycles, vol. 39, No. 1, XP-002607127, 1994, pp. 101-116.

U.S. Appl. No. 13/265,978, filed Oct. 24, 2011, Kozawa, et al.

* cited by examiner

*Primary Examiner* — Janet Andres
*Assistant Examiner* — Timothy R Rozof
(74) *Attorney, Agent, or Firm* — Oblon, Spivak, McClelland, Maier & Neustadt, L.L.P.

(57) ABSTRACT

The invention provides a method for producing 2-azaadamantanes represented by formula (1) in good yields. The method includes cyclizing a compound represented by formula (2) in the presence of an acid.

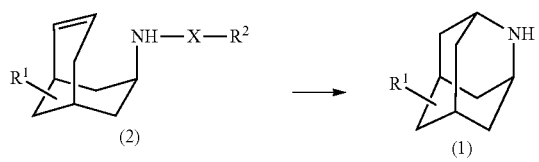

13 Claims, No Drawings

METHOD FOR PRODUCING 2-AZAADAMANTANE

TECHNICAL FIELD

The present invention relates to a novel method for producing a 2-azaadamantane.

BACKGROUND ART

A 2-azaadamantane is useful, for example, as an intermediate for a 2-adamantane-N-oxyl (AZADO) compound to be used as a catalyst for oxidation of an alcohol. As a method for its production, cyclization from an exomethylene form (e.g. Patent Document 1 and Non-Patent Document 1), cyclization from a ketal amide form (e.g. Non-Patent Document 1), cyclization from an azide form (e.g. Non-Patent Document 2), cyclization from an epoxy form (e.g. Non-Patent Documents 2, 3 and 4), cyclization from a diketone form (e.g. Non-Patent Documents 3 and 7), cyclization from a diene from (e.g. Non-Patent Documents 4 and 6) or cyclization of an N-chloroamide form (e.g. Non-Patent Document 5) is, for example, known.

Patent Document 1: WO2006/001387
Non-Patent Document 1: J. Am. Chem. Soc., Vol. 128, No. 26, p. 8412 (2006),
Non-Patent Document 2: J. Chem. Soc., Perkin Trans. I, p. 2529 (1983),
Non-Patent Document 3: J. Org. Chem., Vol. 46, No. 24, p. 4953 (1981),
Non-Patent Document 4: J. Org. Chem., Vol. 46, No. 17, p. 3483 (1981),
Non-Patent Document 5: J. Org. Chem., Vol. 43, No. 19, p. 3750 (1978),
Non-Patent Document 6: Chem. Ber., Vol. 106, p. 339 (1973),
Non-Patent Document 7: Chem. Ber., Vol. 97, p. 3480 (1964).

DISCLOSURE OF THE INVENTION

Problem to be Solved by the Invention

However, in such conventional methods for producing 2-azaadamantanes, a substituent such as an alkyl group, an alcohol group or a halogen group is introduced at the time of the cyclization reaction, and thus a step of removing such a substituent may sometimes be required, and it is obliged to carry out an extra step, thus leading a problem from the viewpoint of the efficiency.

Means to Solve the Problem

The present inventors have conducted an extensive study to solve the above problem and as a result, they have found a novel method for producing a 2-azaadamantane represented by the following formula (1) by a single step reaction by using, as a starting material, a compound represented by the following formula (2) such as a carboxylic acid compound or a sulfonic acid compound and thus have accomplished the present invention. Further, some of the carboxylic acid compounds and sulfonic acid compounds to be used in the method of the present invention are novel compounds not disclosed in the literature, as described hereinafter.

That is, the present invention provides the following.

[1] A method for producing a 2-azaadamantane represented by the following formula (1):

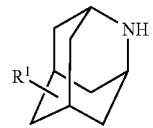

wherein $R^1$ is as defined below, which comprises cyclizing, in the presence of an acid, a compound represented by the following formula (2):

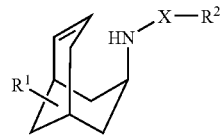

wherein —X—$R^2$ is —C(=O)—$R^2$, —C(=O)—O—$R^2$ or —$SO_2$—$R^2$, and $R^2$ is a hydrogen atom, a $C_{1-12}$ alkyl group which may be substituted by $R^a$, a $C_{1-12}$ cycloalkyl group which may be substituted by $R^a$, a $C_{1-12}$ haloalkyl group, a benzyl group which may be substituted by $R^a$, or an aryl group which may be substituted by $R^a$;

$R^1$ is at least one substituent selected from the group consisting of a hydrogen atom, a halogen atom, a nitro group, a cyano group, a hydroxy group, a mercapto group, an amino group, a formyl group, a carboxyl group, a sulfo group, a $C_{1-12}$ alkyl group, a $C_{3-12}$ cycloalkyl group, a ($C_{1-12}$ alkyl)oxy group, a ($C_{3-12}$ cycloalkyl)oxy group, a ($C_{1-12}$ alkyl)thio group, a ($C_{3-12}$ cycloalkyl)thio group, a ($C_{1-12}$ alkyl)amino group, a ($C_{3-12}$ cycloalkyl)amino group, a di($C_{1-6}$ alkyl)amino group, a di($C_{3-6}$ cycloalkyl)amino group, a ($C_{1-12}$ alkyl) carbonyl group, a $C_{3-12}$ cycloalkylcarbonyl group, a ($C_{1-12}$ alkyl)oxycarbonyl group, a ($C_{3-12}$ cycloalkyl)oxycarbonyl group, a ($C_{1-12}$ alkyl)thiocarbonyl group, a ($C_{3-12}$ cycloalkyl)thiocarbonyl group, a ($C_{1-12}$ alkyl)aminocarbonyl group, a ($C_{3-12}$ cycloalkyl)aminocarbonyl group, a di($C_{1-6}$ alkyl)aminocarbonyl group, a di($C_{3-6}$ cycloalkyl)aminocarbonyl group, a ($C_{1-12}$ alkyl)carbonyloxy group, a ($C_{3-12}$ cycloalkyl)carbonyloxy group, a ($C_{1-12}$ alkyl)carbonylthio group, a ($C_{3-12}$ cycloalkyl)carbonylthio group, a ($C_{1-12}$ alkyl) carbonylamino group, a ($C_{3-12}$ cycloalkyl)carbonylamino group, a di{($C_{1-12}$ alkyl)carbonyl}amino group, a di{($C_{3-12}$ cycloalkyl)carbonyl}amino group, a $C_{1-6}$ haloalkyl group, a $C_{3-6}$ halocycloalkyl group, a $C_{2-6}$ alkenyl group, a $C_{3-6}$ cycloalkenyl group, a $C_{2-6}$ haloalkenyl group, a $C_{3-6}$ halocycloalkenyl group, a $C_{2-6}$ alkynyl group, a $C_{2-6}$ haloalkynyl group, a benzyl group which may be substituted by $R^a$, a benzyloxy group which may be substituted by $R^a$, a benzylthio group which may be substituted by $R^a$, a benzylamino group which may be substituted by $R^a$, a dibenzylamino group which may be substituted by $R^a$, a benzylcarbonyl group which may be substituted by $R^a$, a benzyloxycarbonyl group which may be substituted by $R^a$, a benzylthiocarbonyl group which may be substituted by $R^a$, a benzylaminocarbonyl group which may be substituted by $R^a$, a dibenzylaminocarbonyl group which may be substituted by $R^a$, a benzylcarbonyloxy group which may be substituted by $R^a$, a benzylcarbonylthio group which may be substituted by $R^a$, a benzylcarbonylamino group which may be substituted by $R^a$, a di(benzylcarbonyl)amino group which may be substituted by $R^a$, an aryl group which may be substituted by $R^a$, an aryloxy group which may be substituted by $R^a$, an arylthio group which may be substituted by $R^a$, an arylamino group which may be substituted by $R^a$, a diarylamino group which may be substituted by $R^a$, an arylcarbonyl group which may be substituted by $R^a$, an aryloxycarbonyl group which may be substituted by $R^a$, an arylthiocarbonyl group which may be substituted by $R^a$, an arylaminocarbonyl group which may be substituted by $R^a$, a diarylaminocarbonyl group which may be substituted by $R^a$, an arylcarbonyloxy group which may be substituted by $R^a$, an arylcarbonylthio group which may be substituted by $R^a$, an arylcarbonylamino group which may be substituted by $R^a$, and a di(arylcarbonyl)amino group which may be substituted by $R^a$, and when the number of substituents is two or more, the respective substituents may be the same or different;

$R^a$ is from 1 to 5 substituents selected from the group consisting of a halogen atom, a $C_{1-6}$ alkyl group, a $C_{1-6}$ haloalkyl group, a $C_{3-6}$ cycloalkyl group, a ($C_{1-6}$ alkyl)oxy group, a ($C_{1-6}$ alkyl)oxy ($C_{1-6}$ alkyl) group, a ($C_{1-6}$ alkyl)sulfenyl ($C_{1-4}$ alkyl) group, a $C_{1-6}$ haloalkoxy group, a ($C_{1-4}$ alkyl)sulfenyl group, a ($C_{1-6}$ alkyl)sulfinyl group, a ($C_{1-6}$ alkyl)sulfonyl group, a ($C_{1-6}$ haloalkyl)sulfenyl group, a ($C_{1-6}$ haloalkyl)sulfinyl group, a ($C_{1-6}$ haloalkyl)sulfonyl group, a $C_{2-6}$ alkenyl group, a $C_{2-6}$ haloalkenyl group, a ($C_{2-6}$ alkenyl)oxy group, a ($C_{2-6}$ haloalkenyl)oxy group, a ($C_{2-6}$ alkenyl)sulfenyl group, a ($C_{2-4}$ alkenyl)sulfinyl group, a ($C_{2-6}$ alkenyl)sulfonyl group, a ($C_{2-6}$ haloalkenyl)sulfenyl group, a ($C_{2-6}$ haloalkenyl)sulfinyl group, a ($C_{2-4}$ haloalkenyl)sulfonyl group, a $C_{2-6}$ alkynyl group, a $C_{2-6}$ haloalkynyl group, a ($C_{2-4}$ alkynyl)oxy group, a ($C_{2-6}$ haloalkynyl)oxy group, a ($C_{2-6}$ alkynyl)sulfenyl group, a ($C_{2-6}$ haloalkynyl)sulfinyl group, a ($C_{2-4}$ alkynyl)sulfonyl group, a ($C_{2-4}$ haloalkynyl)phenyl group, a ($C_{2-6}$ haloalkynyl)sulfinyl group, a ($C_{2-6}$ haloalkynyl)sulfonyl group, $NO_2$, CN, a formyl group, OH, SH, $NH_2$, SCN, a ($C_{1-6}$ alkyl)oxycarbonyl group, a ($C_{1-6}$ alkyl)carbonyl group, a ($C_{1-6}$ haloalkyl)carbonyl group, a ($C_{1-6}$ alkyl)carbonyloxy group, a phenyl group, a ($C_{1-4}$ alkyl)amino group and a di($C_{1-4}$ alkyl)amino group, and when the number of substituents is two or more, the respective substituents may be the same or different.

[2] The method according to the above [1], wherein the acid is trifluoromethanesulfonic acid.

[3] The method according to the above [1] or [2], wherein $R^1$ in the formulae (1) and (2) is a hydrogen atom.

[4] The method according to any one of the above [1] to [3], wherein the compound represented by the formula (2) is a compound of the formula (2) wherein —X—$R^2$ is —C(=O)—O—$R^2$, and $R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group which may be substituted by $R^a$, or an aryl group which may be substituted by $R^a$.

[5] The method according to any one of the above [1] to [3], wherein the compound represented by the formula (2) is a compound of the formula (2) wherein —X—$R^2$ is —C(=O)—$R^2$, and $R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group which may be substituted by $R^a$, or an aryl group which may be substituted by $R^a$.

[6] The method according to any one of the above [1] to [3], wherein the compound represented by the formula (2) is a compound of the formula (2) wherein —X—$R^2$ is —$SO_2$—$R^2$, and $R^2$ is a $C_{2-12}$ alkyl group, a $C_{1-12}$ monohaloalkyl group, a $C_{1-12}$ dihaloalkyl group, a benzyl group which may be substituted by $R^a$, or an aryl group which may be substituted by $R^a$.

[7] A compound represented by the formula (2) as defined in the above [1], wherein —X—$R^2$ is —C(=O)—O—$R^2$, and $R^2$ is a $C_{2-12}$ alkyl group, a $C_{3-12}$ cycloalkyl group, a $C_{1-12}$ monohaloalkyl group, a $C_{1-12}$ dihaloalkyl group, a $C_1$ trihaloalkyl group, a $C_{3-12}$ trihaloalkyl group, a benzyl group which may be substituted by $R^a$, or an aryl group which may be substituted by $R^a$.

[8] A compound represented by the formula (2) as defined in the above [1], wherein —X—$R^2$ is —C(=O)—$R^2$, and $R^2$ is a $C_{3-12}$ alkyl group, a $C_{3-12}$ cycloalkyl group, a $C_{1-12}$ haloalkyl group, a benzyl group which may be substituted by $R^a$, or an aryl group (excluding a phenyl group) which may be substituted by $R^a$.

[9] A compound represented by the formula (2) as defined in the above [1], wherein —X—$R^2$ is —$SO_2$—$R^2$, and $R^2$ is a $C_{1-12}$ alkyl group, a $C_{3-12}$ cycloalkyl group, a $C_{1-12}$ haloalkyl group, a benzyl group which may be substituted by $R^a$, or an aryl group which may be substituted by $R^a$.

[10] The compound represented by the formula (2) according to any one of the above [7] to [9], wherein in the formula (2) as defined in claim 1, $R^1$ is a hydrogen atom.

Effect of the Invention

According to the present invention, it is possible to provide a novel method for efficiently producing a 2-azaadamantane in good yield by a small number of steps.

BEST MODE FOR CARRYING OUT THE INVENTION

The method of the present invention is characterized in that a compound represented by the above formula (2) as a starting material, is cyclized to produce a 2-azaadamantane represented by the above formula (1).

The following terms used in the definitions of $R^1$, $R^2$ and $R^a$ in the above formulae (1) and (2) have the following meanings, respectively.

That is, the halogen atom is a fluorine atom, a chlorine atom, a bromine atom or an iodine atom. An expression "halo" also represents such a halogen atom.

Further, "$C_{a-b}$ alkyl" represents a linear or branched alkyl group having from a to b carbon atoms; for example, a methyl group, an ethyl group, a n-propyl group, an i-propyl group, a n-butyl group, an i-butyl group, a s-butyl group, a t-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 1,1-dimethylbutyl group, a 1,3-dimethylbutyl group, a heptyl group, an octyl group, a nonyl group, a decyl group, an undecyl group, a dodecyl group, etc. are mentioned as its specific examples; and it is selected within the range of the specified number of carbon atoms.

Further, "$C_{a-b}$ haloalkyl" represents a linear or branched alkyl group having from a to b carbon atoms, wherein any hydrogen atoms bonded to the carbon atoms are optionally substituted by halogen atoms. In such a case, when hydrogen atoms are substituted by two or more halogen atoms, such halogen atoms may be the same or different from one another. For example, a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a dibromofluoromethyl group, a 2-fluoroethyl group, a 2-chloroethyl group, a 2-bromoethyl group, a 2,2-difluoroethyl group, a 2-chloro-2-fluoroethyl group, a 2,2-dichloroethyl group, a 2-bromo-2-fluoroethyl group, a 2,2,2-trifluoroethyl group, a 2-chloro-2,2-difluoroethyl group, a 2,2-dichloro-2-fluoroethyl group, a 2,2,2-trichloroethyl group, a 2-bromo-2,2-difluoroethyl group, a 2-bromo-2-chloro-2-fluoroethyl group, a 2-bromo-2,2-dichloroethyl group, a 1,1,2,2-tetrafluoroethyl group, a pentafluoroethyl group, a 1-chloro-1,2,2,2-tetrafluoroethyl group, a 2-chloro-1,1,2,2-tetrafluoroethyl group, a 1,2-dichloro-1,2,2-trifluoroethyl group, a 2-bromo-1,1,2,2,-tetrafluoroethyl group, a 2-fluoropropyl group, a 2-chloropropyl group, a 2-bromopropyl group, a 2-chloro-2-fluoropropyl group, a 2,3-dichloropropyl group, a 2-bromo-3-fluoropropyl group, a 3-bromo-2-chloropropyl group, a 2,3-dibromopropyl group, a 3,3,3-trifluoropropyl group, a 3-bromo-3,3-difluoropropyl group, a 2,2,3,3-tetrafluoropropyl group, a 2-chloro-3,3,3-trifluoropropyl group, a 2,2,3,3,3-pentafluoropropyl group, a 1,1,2,3,3,3-hexafluoropropyl group, a heptafluoropropyl group, a 2,3-dichloro-1,1,2,3,3-pentafluoropropyl group, a 2-fluoro-1-methylethyl group, a 2-chloro-1-methylethyl group, a 2-bromo-1-methylethyl group, a 2,2,2-trifluoro-1-(trifluoromethyl)ethyl group, a 1,2,2,2,-tetrafluoro-1-(trifluoromethyl)ethyl group, a 2,2,3,3,4,4-hexafluorobutyl group, a 2,2,3,4,4,4-hexafluorobutyl group, a 2,2,3,3,4,4,4-heptafluorobutyl group, a 1,1,2,2,3,3,4,4-octafluorobutyl group, a nonafluorobutyl group, a 4-chloro-1,1,2,2,3,3,4,4-octafluorobutyl group, a 2-fluoro-2-methylpropyl group, a 2-chloro-1,1-dimethylethyl group, a 2-bromo-1,1-dimethylethyl group, a 5-chloro-2,2,3,4,4,5,5,-heptafluoropentyl group, a tridecafluorohexyl group, etc. are mentioned as its specific examples, and it is selected within the range of the specified number of carbon atoms.

Further, "$C_{a-b}$ cycloalkyl" represents a cyclic alkyl group having from a to b carbon atoms and represents a from 3- to 6-membered single ring or condensed ring structure.

Each ring may be optionally substituted by an alkyl group within the range of the specified number of carbon atoms. For example, a cyclopropyl group, a 1-methylcyclopropyl group, a 2-methylcyclopropyl group, a 2,2-dimethylcyclopropyl group, a 2,2,3,3-tetramethylcyclopropyl group, a cyclobutyl group, a cyclopentyl group, a 2-methylcyclopentyl group, a 3-methylcyclopentyl group, a cyclohexyl group, a 2-methylcyclohexyl group, a 3-methylcyclohexyl group, a 4-methylcyclohexyl group, a bicyclo[2.2.1]heptane-2-yl group, etc. are mentioned as its specific examples, and it is selected within the range of the specified number of carbon atoms.

Further, "$C_{a-b}$ halocycloalkyl" represents a cyclic alkyl group having from a to b carbon atoms, wherein any hydrogen atoms bonded to the carbon atoms are optionally substituted by halogen atoms and represents a from 3- to 6-membered single ring or condensed ring structure. Each ring may optionally be substituted by an alkyl group within the range of the specified number of carbon atoms, and the substitution by the halogen atoms may be at the ring-structure portion or side chain portion, or at both portions. Further, in a case where hydrogen atoms are substituted by two or more halogen atoms, such halogen atoms may be the same or different from one another. For example, a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 2,2,3,3-tetrafluorocyclobutyl group, a 2-(trifluoromethyl)cyclohexyl group, a 3-(trifluoromethyl)cyclohexyl group, a 4-(trifluoromethyl)cyclohexyl group, etc. are mentioned as its specific examples, and it is selected within the range of the specified number of carbon atoms.

Further, "$C_{a-b}$ alkenyl" represents a linear or branched alkenyl group having from a to b carbon atoms and having one or more double bonds in its molecule; for example, a vinyl group, a 1-propenyl group, a 2-propenyl group, a 1-methylethenyl group, a 2-butenyl group, a 1-methyl-2-propenyl group, a 2-methyl-2-propenyl group, a 2-pentenyl group, a 2-methyl-2-butenyl group, a 3-methyl-2-butenyl group, a 2-ethyl-2-propenyl group, a 1,1-dimethyl-2-propenyl group, a 2-hexenyl group, a 2-methyl-2-pentenyl group, a 2,4-dimethyl-2,6-heptadienyl group, a 3,7-dimethyl-2,6-octadienyl group, etc. are mentioned as its specific examples; and it is selected within the range of the specified number of carbon atoms.

Further, "$C_{a-b}$ haloalkenyl" represents a linear or branched alkenyl group having from a to b carbon atoms and having one or more double bonds in its molecule, wherein any hydrogen atoms bonded to the carbon atoms are optionally substituted by halogen atoms. In such a case, when hydrogen atoms are substituted by two or more halogen atoms, such halogen atoms may be the same or different from one another. For example, 2,2-dichlorovinyl group, a 2-fluoro-2-propenyl group, a 2-chloro-2-propenyl group, a 3-chloro-2-propenyl group, a 2-bromo-2-propenyl group, a 3-bromo-2-propenyl group, a 3,3-difluoro-2-propenyl group, a 2,3-dichloro-2-propenyl group, a 3,3-dichloro-2-propenyl group, a 2,3-dibromo-2-propenyl group, a 2,3,3-trifluoro-2-propenyl group, a 2,3,3-trichloro-2-propenyl group, a 1-(trifluoromethyl)ethenyl group, a 3-chloro-2-butenyl group, a 3-bromo-2-butenyl group, a 4,4-difluoro-3-butenyl group, a 3,4,4-trifluoro-3-butenyl group, a 3-chloro-4,4,4-trifluoro-2-butenyl group, a 3-bromo-2-methyl-2-propenyl group, etc. are mentioned as its specific examples, and it is selected within the range of the specified number of carbon atoms.

Further, "$C_{a-b}$ cycloalkenyl" represents a cyclic alkenyl group having from a to b carbon atoms and having one or more double bonds, and represents a from 3- to 6-membered single ring or condensed ring structure. Further, each ring may optionally be substituted by an alkyl group within the range of the specified number of carbon atoms, and further, the double bond may be endo- or exo-. For example, 2-cyclopenten-1-yl group, a 3-cyclopenten-1-yl group, a 2-cyclohexen-1-yl group, a 3-cyclohexen-1-yl group, a bicyclo[2.2.1]-5-hapten-2-yl group, etc. are mentioned as its specific examples, and it is selected within the range of the specified number of carbon atoms.

Further, "$C_{a-b}$ halocycloalkenyl" represents a cyclic alkenyl group having from a to b carbon atoms and having one or more double bonds, wherein any hydrogen atoms bonded to the carbon atoms are optionally substituted by halogen atoms, and represents a from 3- to 6-membered single ring or condensed ring structure. Further, each ring may optionally be substituted by an alkyl group within the range of the specified number of carbon atoms, and further, the double bond may be endo- or exo-. Further, the substitution by halogen atoms may be at the ring structure portion or side chain portion, or at both portions, and when hydrogen atoms are substituted by two or more halogen atoms, such halogen atoms may be the same or different from one another. For example, a 2-chlorobicyclo[2.2.1]-5-hapten-2-yl group, etc. are mentioned as its specific examples, and it is selected within the range of the specified number of carbon atoms.

Further, "$C_{a-b}$ alkynyl" represents a linear or branched alkynyl group having from a to b carbon atoms and having one or more triple bonds in its molecule. For example, an ethynyl group, a 1-propynyl group, a 2-propynyl group, a 2-butynyl group, a 1-methyl-2-propynyl group, a 2-pentynyl group, a 1-methyl-2-butynyl group, a 1,1-dimethyl-2-propynyl group, a 2-hexynyl group, etc. are mentioned as its specific examples, and it is selected within the range of specified number of carbon atoms.

Further, "$C_{a-b}$ haloalkynyl" represents a linear or branched alkynyl group having from a to b carbon atoms and having one or more triple bonds in its molecule, wherein any hydrogen atoms bonded to the carbon atoms are optionally substituted by halogen atoms. In such a case, when hydrogen atoms are substituted by two or more halogen atoms, such halogen atoms may be the same or different from one another. For example, a 2-chloroethynyl group, a 2-bromoethynyl group, a 2-iodoethynyl group, a 3-chloro-2-propynyl group, a 3-bromo-2-propynyl group, a 3-iodo-2-propynyl group, etc. are mentioned as its specific examples, and it is selected within the range of the specific number of carbon atoms.

Further, the aryl group which may be substituted by $R^a$ may, for example, be a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 4-iodophenyl group, a 2,4-dichlorophenyl group, a 3,4-dichlorophenyl group, a 2,6-difluorophenyl group, a 2,6-dichlorophenyl group, a 2-fluoro-4-chlorophenyl group, a 2,3,4,5,6-pentafluorophenyl group, a 2-methylphenyl group, 3-methylphenyl group, a 4-methylphenyl group, a 2,5-dimethylphenyl group, a 4-methyl-2,3,5,6-tetrafluorophenyl group, a 2-methoxyphenyl group, a 3-methoxyphenyl group, a 4-methoxyphenyl group, a 2,6-dimethoxyphenyl group, a 3,4-dimethoxyphenyl group, a 3,4,5-trimethoxyphenyl group, a 2-trifluoromethylphenyl group, a 3-trifluoromethylphenyl group, a 4-trifluoromethylphenyl group, a 2-nitrophenyl group, a 3-nitrophenyl group, a 4-nitrophenyl group, a 2-cyanophenyl group, a 3-cyanophenyl group, a 4-cyanophenyl group, an α-naphthyl group, a 8-naphthyl group, a o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-R-phenanthryl group, a 4-phenanthryl group, a 9-phenanthryl group, a 2-thienyl group, a 3-thienyl group, a 2-furyl group, a 3-furyl group, a 2-pyranyl group, a 3-pyranyl group, a 4-pyranyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-pyrrolyl group, a 2-pyrrolyl group, a 3-pyrrolyl group, a 1-imidazolyl group, 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isooxazolyl group, a 4-isooxazolyl group, a 5-isooxazolyl group, a 2-pyridyl group, a 3-pyridyl group, a 4-pyridyl group, a 2-pyradinyl group, a 2-pyrimidinyl group, a 4-pyrimidinyl group, a 5-pyrimidinyl group, a 3-pyridazinyl group, a 4-pyridazinyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 2-naphthyridinyl group, a 3-naphthyridinyl group, a 4-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-ptenidinyl group, a 4-ptenidinyl group, a 6-ptenidinyl group, a 7-ptenidinyl group or a 3-furazanyl group.

Further, the benzyl group which may be substituted by $R^a$ may, for example, be a benzyl group, a 2-methylbenzyl group, a 3-methylbenzyl group, a 4-methylbenzyl group, a 2-chlorobenzyl group, a 3-chlorobenzyl group, a 4-chlorobenzyl group, a 2-fluorobenzyl group, a 4-fluorobenzyl group, a 2-methoxybenzyl group, a 4-methoxybenzyl group, a 4-nitrobenzyl group or a 4-cyanobenzyl group.

As a preferred group for $R^1$, a hydrogen atom, a halogen atom or a $C_{1-12}$ alkyl group may be mentioned. The most preferred group for $R^1$ is a hydrogen atom or a $C_{1-4}$ alkyl group.

Further, among acid compounds represented by the above formula (2) to be used as a starting material in the method of the present invention, the following three types of compounds are novel compounds not disclosed in the literature.

A compound of the formula (2), wherein —X—$R^2$ is —C(=O)—O—$R^2$, and $R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group which may be substituted by $R^a$, or an aryl group which may be substituted by $R^a$. Particularly, a compound wherein $R^2$ is a benzyl group or methyl.

A compound of the formula (2), wherein —X—$R^2$ is —C(=O)—$R^2$, and $R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group which may be substituted by $R^a$, or an aryl group which may be substituted by $R^a$. Particularly, a compound wherein $R^2$ is a methyl group.

A compound of the formula (2), wherein —X—$R^2$ is —$SO_2$—$R^2$, and $R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group which may be substituted by $R^a$, or an aryl group which may be substituted by $R^a$. Particularly, a compound wherein $R^2$ is a toluoyl group or a phenyl group.

The method of the present invention can be carried out, for example, in accordance with the following scheme, including the production of the starting material.

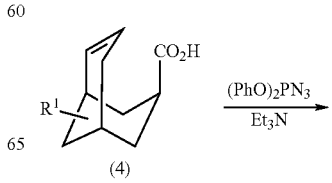

(4)

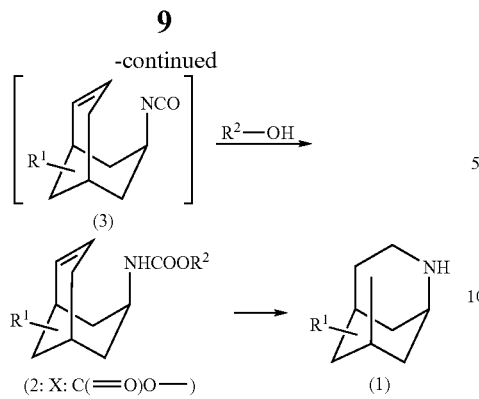

(3)

(2: X: C(=O)O—)    (1)

In the above scheme, the method for producing the compound (3) from the compound (4) can be carried out in accordance with the method disclosed in J. Chem. Soc. Perkin Trans. I, p. 2529 (1983). Further, the alcohol (R²OH) to be used for the reaction to obtain the compound (2) as a starting material in the method of the present invention from the compound (3), is usually used in an amount of preferably from 0.1 to 100 equivalents, more preferably from 1 to 20 equivalents, per one equivalent of the compound (3). It is also possible to produce the compound (2) from the compound (4) without isolating the compound (3) after forming the compound (3) from the compound (4).

In the present invention, in the step of producing the compound (1) from the compound (2) in the presence of an acid, the amount of the acid to be used is usually preferably from 0.001 to 100 equivalents, more preferably from 2 to 5 equivalents, per one equivalent of the compound (2).

The acid to be used may, for example, be an inorganic acid such as sulfuric acid or phosphoric acid; an organic acid such as acetic acid, trifluoroacetic acid, methanesulfonic acid, trifluoromethanesulfonic acid, p-toluenesulfonic acid, phenol, pentafluorophenol, 2,4-dinitrophenol, trifluoromethanesulfonyl imide or 1-[bis(trifluoromethanesulfonyl)methyl]-2,3,4,5,6-pentafluorobenzene; a metal chloride such as boron trifluoride, aluminum trichloride, tin tetrachloride, magnesium dichloride, iron trichloride or titanium tetrachloride; a metal alkoxide such as triisopropoxy aluminum, diethoxy magnesium or tetraisopropoxy titanium; or a metal triflate such as bis(trifluoromethanesulfonyl)tin, bis(trifluoromethanesulfonyl)copper or tris(trifluoromethanesulfonyl)scandium. Among them, trifluoromethanesulfonic acid is preferred.

In a case where in the above scheme, the 2-azaadamantane represented by the formula (1) is produced from the compound (2) by a cyclization reaction in the presence of the acid, the compound (2) and the acid are mixed and reacted at a temperature of preferably from −80° C. to the boiling point of the solvent, particularly preferably from −5° C. to 10° C., preferably with stirring, preferably for from 1 to 5 hours. The reaction is carried out preferably by using a solvent.

Upon completion of the reaction, neutralization is carried out to obtain a 2-azaadamantane as the desired product. The 2-azaadamantane may be isolated by concentration and drying, as the case requires. Further, the obtained 2-azaadamantane may be purified to increase the purity by acid/base extraction, as the case requires.

In the present invention, in a case where X in the formula (2) is SO₂— or C(=O)—, in accordance with the following scheme, the compound represented by the formula (4) is led to a compound represented by the formula (5), and then by means of a known amino group-protecting means, it is possible to obtain a compound represented by the formula (2) as a starting material in the method of the present invention.

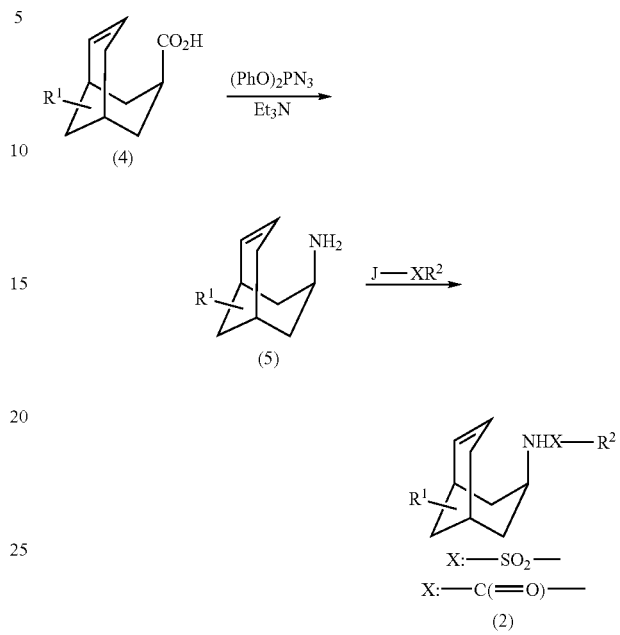

In the above scheme, J in J-XR² is a leaving group such as a halogen atom or an alkylcarbonyloxy group. XR² is C(=O)—R² or SO₂—R², and R² is a linear or branched $C_{1\text{-}12}$ alkyl group, a $C_{3\text{-}12}$ cycloalkyl group, a $C_{2\text{-}12}$ haloalkyl group, a benzyl group which may be substituted by $R^a$, or an aryl group which may be substituted by $R^a$. Among them, preferred is a known protective group for an amino group, such as an alkylcarbonyl group (such as an acetyl group, a propionyl group or a butyryl group), a formyl group, a phenylcarbonyl group, a p-toluenesulfonyl group, a trifluoromethanesulfonyl group or a methanesulfonyl group. Further, as J-XR², it is also possible to employ an acid anhydride.

As a means to change the compound represented by the formula (5) to the compound represented by the formula (2), a known protecting means for an amino group may be employed. As such a method, a method disclosed in Protective Groups in Organic Chemistry (J. F. W. McOmie et al., Plenum Press; Protective Groups in Organic Synthesis, 3rd Edition (Theodora W. Greene, Peter G. M. Wuts, John Wiley & Sons, Inc. (ISBN: 0-471-16019-9), April 1999, may, for example, be mentioned.

Further, the carboxylic acid compound represented by the formula (4) can be produced in accordance with the following scheme, for example, by a method in accordance with the method disclosed in J. Org. Chem., Vol. 39, No. 26, p. 3822 (1974).

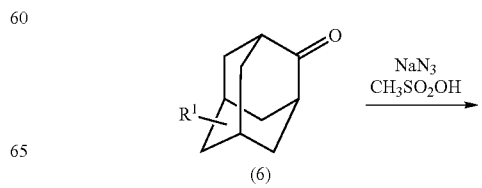

-continued

In the above scheme, it is also possible to produce the compound (4) in one step without isolating the compound (7) after leading the compound (6) to the compound (7). In such a case, for example, after carrying out the reaction from the compound (6) to the compound (7), an aqueous solution of an alkali metal hydroxide may be added to the reaction solution, whereby the compound (4) can be obtained. In the above scheme, Ms- represents $CH_3SO_2$—.

In the present invention, the solvent to be used to carry out each reaction in each of the above schemes is preferably one which is stable in the respective reaction conditions and which is inert to the reaction and does not hinder the reaction. Such a solvent may, for example, be water, an alcohol (such as methanol, ethanol, propanol, butanol or octanol), a cellosolve (such as methoxyethanol or ethoxyethanol), an aprotic polar organic solvent (such as dimethylformamide, dimethylsufoxide, dimethylacetamide, tetramethylurea, sulforane, N-methylpyrrolidone or N,N-dimethylimidazolidinone), an ether (such as diethyl ether, diisopropyl ether, t-butyl methyl ether, tetrahydrofuran or dioxane), an aliphatic hydrocarbon (such as pentane, hexane, c-hexane, octane, decane, decalin or petroleum ether), an aromatic hydrocarbon (such as benzene, chlorobenzene, o-dichlorobenzene, nitrobenzene, toluene, xylene, mesitylene or tetralin), a halogenated hydrocarbon (such as chloroform, dichloromethane, dichloroethane or carbon tetrachloride), a ketone (such as acetone, methyl ethyl ketone, methyl butyl ketone or methyl isobutyl ketone), a lower fatty acid ester (such as methyl acetate, ethyl acetate, butyl acetate or methyl propionate), an alkoxy alkane (such as dimethoxyethane or diethoxyethane) or a nitrile (such as acetonitrile, propionitrile or butyronitrile). Such solvents are suitably selected in view of the efficiency for the reaction and may be used alone or in combination as mixed. Further, in some cases, a suitable dehydrating agent or a drying agent may be used for a non-aqueous solvent.

In the present invention, the desired product in each step in the above schemes, can be purified by means of a usual purification means such as extraction, distillation, recrystallization or column chromatography, or it may be supplied as a starting material for the next step as a crude product without purification.

Thus, according to the present invention, a 2-azaadamantane represented by the formula (1) as the desired product can be produced in good yield, although the yield may be different also depending upon the specific 2-azaadamantane compound, and for example, in the case of 2-azaadamantane disclosed in Examples, it can be produced in good yield of 90% from the compound of the formula (2).

EXAMPLES

Now, the present invention will be described in detail with reference to Examples, but is should be understood that the present invention is by no means thereby restricted.

Starting Material Preparation Example 1

Preparation of endo-bicyclo[3.3.1]non-6-ene-3-carboxylic acid

Into a 1 L three-necked flask, 48.0 g (0.320 mol) of 2-adamantanone and 300 g (202 mL, 1.58 M) of methanesulfonic acid were added and dissolved. To this solution, 22.9 g (0.353 mol) of sodium azide was gradually added with stirring so that the temperature of the reaction solution was maintained to be from 20° C. to 35° C. In the process, hydrazoic acid and nitrogen gas were generated, and the reaction temperature was optionally lowered by cooling with ice or water bath. Thereafter, stirring was carried out at room temperature for one hour, and disappearance of 2-adamantanone was confirmed by gas chromatography. At that time, formation of 4-methanesulfonyl-2-adamantanone was confirmed. Then, a Dimroth condenser was connected to the reaction apparatus, and a 50 mass % potassium hydroxide aqueous solution (450 mL) was gradually added. At that time, the reaction temperature rose to 95° C. The reaction solution was left to cool with stirring as it was at room temperature for 1.5 hours, and then, the reaction solution was washed with 600 mL of diethyl ether. To the aqueous layer, 120 mL of concentrated hydrochloric acid was carefully added to acidify the reaction solution, whereby the desired product was crystallized. It was collected by filtration, thoroughly washed with water and then dried to obtain 36.5 g (0.220 mol, 69%) of crude endo-bicyclo[3.3.1]non-6-ene-3-carboxylic acid.

Endo-bicyclo[3.3.1]non-6-ene-3-carboxylic acid: $^1$H-NMR (400 MHz, $CDCl_3$): d 5.65 (m, 1H), 5.58 (dt, J=9.5, 3.2 Hz, 1H), 2.57 (t, J=6.3 Hz, 1H), 2.39 (d, J=14.0 Hz, 1H), 2.36-2.20 (m, 4H), 2.06 (br s, 1H), 1.78-1.66 (m, 3H), 1.54 (br d, J=12.3 Hz, 1H). $_{13}$C-NMR (100 MHz, $CDCl_3$): d 182.6, 130.6, 129.5, 35.9, 31.9, 31.4, 31.1, 29.8, 28.5, 26.2. IR (neat, $cm_{-1}$): 1680. MS m/z: 166 ($M_+$), 79 (100%). HRMS (EI): Calcd. for $C_{10}H_{14}O_2$ 166.0994 ($M^+$). found: 166.0989.

Starting Material Preparation Example 2

Preparation of N-benzyloxycarbonyl-endo-bicyclo [3.3.1]non-6-en-3-ylamine

To a 1 L eggplant-form flask, 14.7 g (88.5 mmol) of endo-bicyclo[3.3.1]non-6-ene-3-carboxylic acid obtained in Starting Material Preparation Example 1, and tetrahydropyran (88.5 mL, 1.0 M) were added and dissolved, and 29.8 mL (213 mmol) of triethylamine and 21.0 mL (97.4 mmol) of diphenylphosphoryl azide (DPPA) were sequentially added at room temperature, followed by stirring for 3 hours at the same temperature. At that time, endo-bicyclo[3.3.1]non-6-ene-3-carbonylazide was formed in the reaction system.

$^1$H-NMR (400 MHz, $CDCl_3$): d 5.67 (m, 1H), 5.61 (dt, J=9.9, 3.1 Hz, 1H), 2.53 (t, J=6.6 Hz, 1H), 2.43 (d, J=14.2 Hz, 1H), 2.37-2.13 (m, 4H), 2.07 (br s, 1H), 1.79 (dd, J=6.4, 3.6 Hz, 1H) 1.76-1.65 (m, 2H), 1.54 (br d, J=12.3 Hz, 1H). $_{13}$C-NMR (100 MHz, $CDCl_3$): d 183.0, 130.5, 129.4, 39.0, 31.9, 31.4, 31.0, 30.2, 28.4, 26.2. IR (neat, $cm_{-1}$): 2136, 1710, 1192, 1041. MS m/z: 191 ($M_+$), 79 (100%). HRMS (EI): Calcd. for $C_{10}H_{13}N_3O$ 191.1059 ($M^+$). found: 191.1049.

To this reaction solution, 88.5 mL of tetrahydropyran and 91.6 mL (885 mmol) of benzyl alcohol were added, followed by heating and refluxing until disappearance of endo-bicyclo [3.3.1]non-6-ene-3-carbonylazide was confirmed. After the reaction solution was left to cool, water and ethyl acetate were added for liquid separation. The organic layer was washed with a saturated sodium chloride aqueous solution, dried over magnesium sulfate and concentrated. The crude product was subjected to column chromatography (eluent: ethyl acetate/hexane (1:8 v/v)) to obtain 20.4 g (85%) of N-benzyloxycarbonyl-endo-bicyclo[3.3.1]non-6-en-3-ylamine.

N-benzyloxycarbonyl-endo-bicyclo[3.3.1]non-6-en-3-ylamine: $^1$H-NMR (400 MHz, $CDCl_3$): d 7.38-7.25 (m, 5H), 6.05 (t, J=7.8 Hz, 1H), 5.92 (d, J=8.4 Hz, 1H), 5.79 (dt, J=9.9, 3.2 Hz, 1H), 5.08 (d, J=12.4 Hz, 1H), 5.03 (d, J=12.4 Hz, 1H), 4.03 (m, 1H), 2.43 (dd, J=18.8, 7.2 Hz, 1H), 2.34 (br s, 1H), 2.18 (br s, 1H), 2.06 (br d, J=18.1 Hz 1H), 2.00 (dt, J=14.7, 5.5 Hz, 1H) 1.89-1.66 (m, 4H), 1.55 (br d, J=12.1 Hz, 1H). $_{13}$C-NMR (100 MHz, CDCl$_3$): d 155.5, 136.9, 134.4, 128.8, 128.4, 128.0, 127.9, 66.2, 44.7, 37.5, 34.2, 32.5, 31.0, 27.7, 25.5. IR (neat, cm$_{-1}$): 3434, 1721, 1504. MS m/z: 271 (M$_+$), 91 (100%). HRMS (EI): Calcd. for C$_{17}$H$_{21}$NO$_2$ 271.1572 (M$^+$). found: 271.1554.

Example 1

Preparation of 2-azaadamantane

In a 100 ml eggplant-form flask, a methylene chloride (40 ml, 0.4 M) solution containing 4.2 g (15.5 mmol) of N-benzyloxycarbonyl-endo-bicyclo[3.3.1]non-6-en-3-ylamine obtained in Starting Material Preparation Example 2 was prepared. To the solution, 5.8 ml (62 mmol) of trifluoromethanesulfonic acid was added under cooling with ice, followed by stirring for one-hour. After confirming disappearance of the starting material by thin-layer chromatography (TLC), 9.6 ml (68.2 mmol) of triethylamine was added under cooling with ice for neutralization. Then, a 10 mass % sodium hydroxide aqueous solution (40 ml) was added, followed by stirring for one hour. Then, chloroform was added for extraction, and the extract solution was dried over magnesium sulfate and concentrated by an evaporator to obtain crude 2-azaadamantane.

2-azaadamantane: $^1$H-NMR (400 MHz, CDCl$_3$): d 3.13 (s, 2H), 2.04 (s, 2H), 1.94 (d, J=11.4 Hz, 4H), 1.87 (s, 2H), 1.77 (d, J=11.4 Hz, 4H).

Reference Example 1

Preparation of 2-azaadamantane-N-oxyl (AZADO)

To a methanol (31 ml, 0.5 M) and methylene chloride (10 ml) solution containing 9.7 g (70 mmol) of crude 2-azaadamantane obtained in Example 1 and 2.6 g (7.75 mmol) of sodium tungstate dihydrate, 5.8 g (62 mmol) of UHP (urea-hydrogen peroxide) was added, followed by stirring at room temperature for 3 hours. After confirming the termination of the reaction, water (80 ml) was added, followed by extraction with chloroform. The organic layer was dried over magnesium sulfate, and then, the solvent was distilled off under reduce pressure. The residue was subjected to silica gel column chromatography (eluent: ethyl acetate/hexane (1:8 v/v)), whereby from the eluate, AZADO (2.12 g, 13.9 mmol, in a yield of 89.8% from N-benzyloxycarbonyl-endo-bicyclo[3.3.1]non-6-en-3-ylamine) was obtained as a red solid. Various data agreed to one synthesized by a known synthesis method.

Elemental analysis (C$_9$H$_{14}$NO) Calcd. for C, 9.27; H, 71.02; N, 9.20. found: H, 9.18; C, 71.06; N, 9.13.

Sublimation point: 1,600 Pa, 48° C.

Preparation Examples of Other Starting Materials

Now, Preparation Examples of other starting materials to be used in the present invention will be described. The relations of the starting material compounds to be used here, are as shown below. Further, abbreviations in the compounds have the following meanings, respectively.

Ts: toluenesulfonyl, Ac: acetyl, Et: ethyl, Me: methyl, and Tf: trifluoromethanesulfonyl

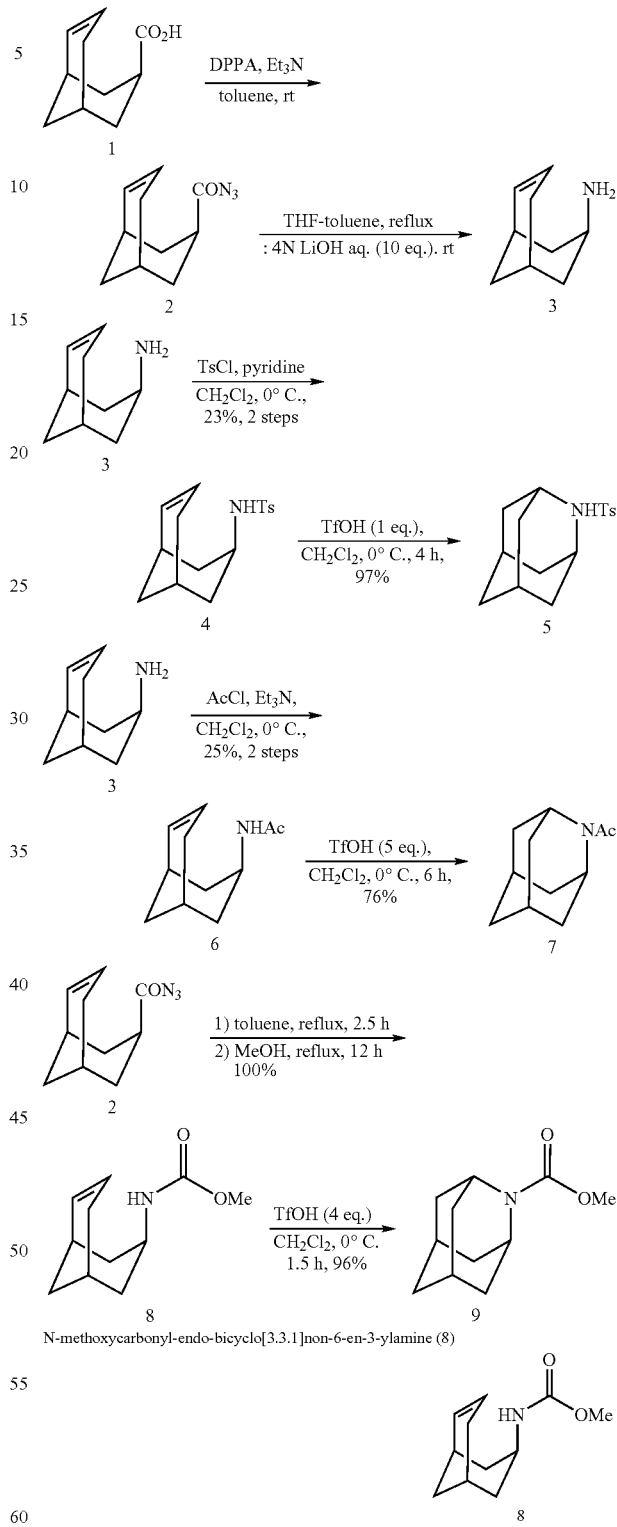

1. Preparation of endo-bicyclo[3.3.1]non-6-en-3-ylamine (3) and N-p-toluenesulfonyl-endo-bicyclo [3.3.1]non-6-en-3-ylamine (4)

A tetrahydrofuran (82 mL, 0.2 M)/toluene (20 mL) solution containing 3.14 g (16.4 mmol) of endo-bicyclo[3.3.1]

non-6-ene-3-carbonylazide (2) was heated and refluxed until disappearance of the starting material was confirmed. After the solution was left to cool, a 4M lithium hydroxide aqueous solution (41.1 mL, 164 mmol) was added, followed by stirring for 9 hours. Tetrahydrofuran was distilled off under reduced pressure, and then, $CHCl_3$ was added for extraction. The extract was dried over $K_2CO_3$, and then, the solvent was distilled off under reduced pressure to obtain 1.23 g of crude amine (3). This compound was used for the next reaction without purification.

To a $CH_2Cl_2$ (3.8 ml, 10 ml eggplant-form flask) solution of the crude amine (3) (105 mg), pyridine (0.185 mL, 2.29 mmol) and p-toluenesulfonyl chloride (218 mg, 1.14 mmol) were sequentially added under cooling with ice, followed by stirring for 18 hours under cooling with ice. $H_2O$ was added under cooling with ice, and the solution was extracted with AcOEt, and then, the organic layer was dried over $MgSO_4$, and the solvent was distilled off under reduced pressure. The residue was subjected to flash silica gel chromatography, whereby from the AcOEt-hexane (1:15 v/v) eluate, sulfonamide (4) (92.0 mg, 0.316 mmol, 23%, 2 steps) was obtained.

N-p-toluenesulfonyl-endo-bicyclo[3.3.1]non-6-en-3-ylamine (4): $^1$H-NMR (400 MHz, $CDCl_3$): δ7.70 (d, J=8 Hz, 2H), 7.28 (d, J=8 Hz, 2H), 6.03 (m, 1H), 5.83 (dt, J=10, 3.5 Hz, 1H), 5.76 (d, J=10 Hz, 1H), 3.62 (m, 1H), 2.46-2.35 (m, 1H), 2.26 (br s, 1H), 2.16-2.04 (m, 2H), 1.86 (dt, J=15, 5.6 Hz, 1H), 1.76 (dt, J=15, 2.0 Hz, 1H), 1.70-1.60 (m, 2H), 1.56 (dt, J=14, 2.3 Hz, 1H), 1.40 (d, J=12 Hz, 1H). $^{13}$C-NMR (100 MHz, $CDCl_3$): 6142.8, 138.6, 134.5, 129.5, 129.2, 126.8, 47.7, 37.6, 34.3, 32.1, 30.8, 27.5, 25.3, 21.4. IR (neat, cm$^{-1}$): 3349, 1308, 1157. MS m/z: 291 (M*), 136 (100%). HRMS (EI): Calcd. for $C_{16}H_{21}NO_2S$: 291.1293 (M$^+$). found: 291.1314.

2. Preparation of N-acetyl-endo-bicyclo[3.3.1]non-6-en-3-ylamine (6)

Into a $CH_2Cl_2$ (3.8 ml, 10 ml eggplant-form flask) solution of the crude amine (3) (101 mg), $Et_3N$ (0.322 mL, 2.29 mmol) and acetyl chloride (81 mg, 1.14 mmol) were sequentially added under cooling with ice, followed by stirring for 8 hours under cooling with ice. After confirming disappearance of the starting material by TLC, $H_2O$ was added under cooling with ice, followed by extraction with AcOEt. The organic layer was dried over $MgSO_4$, and the solvent was distilled off under reduced pressure. The reside was subjected to flash silica gel chromatography, whereby from the AcOEt-hexane (1:1 v/v) eluate, an amide (6) (63.2 mg, 0.353 mmol, 25%, 2 steps) was obtained.

N-acetyl-endo-bicyclo[3.3.1]non-6-en-3-ylamine (6): $^1$H-NMR (400 MHz, $CDCl_3$): δ6.74 (br s, 1H), 6.11 (m, 1H), 5.83 (m, 1H), 4.28 (m, 1H), 2.47 (dd, J=19, 7.1 Hz, 1H), 2.37 (br s, 1H), 2.20 (br s, 1H), 2.06 (br d, J=19 Hz, 1H), 1.96 (m, 1H), 1.86 (s, 3H), 1.83 (s, 2H), 1.57 (d, J=12 Hz, 1H). $^{13}$C-NMR (100 MHz, $CDCl_3$): δ 168.1, 134.8, 128.7, 42.6, 37.1, 33.8, 32.6, 30.8, 27.7, 25.4, 23.5. IR (neat, cm$^1$): 3352, 1636. MS m/z: 179 (M$^+$), 179 (100%). HRMS (EI): Calcd. for $C_{11}H_{17}NO$: 179.1310 (M$^+$). found: 179.1299.

3. Preparation of N-p-toluenesulfonyl-2-azaadamantane (5)

To a $CH_2Cl_2$ (1.0 ml, 0.1 M, 10 ml eggplant-form flask) solution containing 30.3 mg (0.104 mmol) of the sulfonamide (4), trifluoromethanesulfonic acid (9.2 μL, 0.104 mmol) was added under cooling with ice, followed by stirring for 4 hours. After confirming disappearance of the starting material by TLC, a saturated $NaHCO_3$ aqueous solution was added under cooling with ice, followed by extraction with AcOEt. The organic layer was dried over $MgSO_4$, and the solvent was distilled off under reduced pressure. The residue was subjected to flash silica gel chromatography, whereby from the AcOEt-hexane (1:15 v/v) eluate, N-p-toluenesulfonyl-2-azaadamantane (5) (29.3 mg, 0.101 mmol, 97%) was obtained.

N-p-toluenesulfonyl-2-azaadamantane (5): $^1$H-NMR (400 MHz, $CDCl_3$): δ7.73 (d, J=8 Hz, 2H), 7.27 (d, J=8 Hz, 2H), 4.12 (s, 2H), 2.41 (s, 3H), 2.00 (br s, 2H), 1.87-1.75 (m, 6H), 1.64 (d, J=12 Hz, 4H). $^{13}$C-NMR (100 MHz, $CDCl_3$): δ 142.6, 139.0, 129.5, 127.0, 48.8, 35.5, 35.0, 26.4, 21.4. IR (neat, cm$^{-1}$): 1341, 1161. MS m/z: 291 (M$^+$), 291 (100%). HRMS (EI): Calcd. for $C_{16}H_{21}NO_2S$: 291.1293 (M$^+$). found: 291.1277.

4. Preparation of N-acetyl-2-azaadamantane (7)

To a $CH_2Cl_2$ (1.7 ml, 0.1 M, 10 ml eggplant-form flask) solution containing 31.1 mg (0.174 mmol) of the amide (6), trifluoromethanesulfonic acid (77 μL, 0.870 mmol) was added under cooling with ice, followed by stirring for 4 hours. After confirming disappearance of the starting material by TLC, a saturated $NaHCO_3$ aqueous solution was added under cooling with ice, followed by extraction with AcOEt. The organic layer was dried over $MgSO_4$, and the solvent was distilled off under reduced pressure. The residue was subjected to flash silica gel chromatography, whereby from the AcOEt-hexane (1:1 v/v) eluate, N-acetyl-2-azaadamantane (7) (23.8 mg, 0.133 mmol, 76%) was obtained.

N-acetyl-2-azaadamantane (7): $^1$H-NMR (400 MHz, $CDCl_3$): δ 4.84 (br s, 1H), 3.99 (br s, 1H), 2.09 (br s, 2H), 2.06 (s, 3H), 1.88 (br s, 2H), 1.81 (m, 6H), 1.75 (br d, J=13 Hz, 2H). $^{13}$C-NMR (100 MHz, $CDCl_3$): 6167.4, 49.9, 43.8, 36.1, 35.5, 35.3, 26.5, 21.2. IR (neat, cm$^{-1}$): 1,633. MS m/z: 179 (M$^+$), 179 (100%). HRMS (EI): Calcd. for $C_{11}H_{17}NO$: 179.1310 (M$^+$). found: 179.1292.

5. Preparation of N-methoxycarbonyl-endo-bicyclo [3.3.1]non-6-en-3-ylamine (8)

A toluene (5.65 mL, 0.2 M, 30 mL eggplant-form flask) solution containing 216 mg (1.13 mmol) of acylazide (2) was heated and refluxed for two hours. After confirming disappearance of the starting material, the solvent was distilled off under reduced pressure. To the residue, 5.65 mL (0.2 M) of methanol was added, followed by heating and refluxing for 12 hours. The solvent was distilled off under reduced pressure, and the residue was subjected to flash silica gel column chromatography, whereby from the AcOEt-hexane (1:8 v/v) eluate, methyl carbamate (8) (222 mg, 1.14 mmol, 100%) was obtained as colorless oil.

$^1$H-NMR (400 MHz, $CDCl_3$): δ 6.07 (t, J=6.52 Hz, 1H), 5.88 (br s, 1H), 5.81 (dt, J=9.66, 3.38 Hz, 1H), 4.01 (m, 1H), 2.44 (dd, J=18.8, 7.00 Hz, 1H), 2.35 (br s, 1H), 2.19 (br s, 1H), 2.08 (br d, J=18.6 Hz, 1H), 1.98 (dt, J=14.7, 5.55 Hz, 1H), 1.89-1.66 (m, 4H), 1.55 (d, J=11.8 Hz, 1H). $^{13}$C-NMR (100 MHz, $CDCl_3$): δ 156.0, 134.5, 128.7, 51.6, 44.6, 37.6, 34.2, 32.5, 31.0, 27.7, 25.5. IR (neat, cm$^{-1}$): 3,437, 1,730. MS m/z: 195 (M$^+$), 79 (100%). HRMS (EI): Calcd. for $C_{11}H_{17}NO$ 195.1259 (M$^+$). found: 195.1238.

6. Preparation of N-methoxycarbonyl-2-azaadamantane (9)

To a $CH_2Cl_2$ (1.37 ml, 0.2 M, 10 ml eggplant-form flask) solution containing 53.5 mg (0.274 mmol) of methyl carbamate (8), trifluoromethanesulfonic acid (97 µL, 1.10 mmol) was added under cooling with ice, followed by stirring for 4 hours. After confirming disappearance of the starting material by TLC, a saturated NaHCO$_3$ aqueous solution was added under cooling with ice, followed by extraction with AcOEt. The organic layer was dried over MgSO$_4$, and the solvent was distilled off under reduced pressure. The residue was subjected to flash silica gel column chromatography, whereby from the AcOEt-hexane (1:8 v/v) eluate, N-methoxycarbonyl-2-azaadamantane (9) (51.2 mg, 0.262 mmol, 96%) was obtained as white solid. A part thereof was recrystallized from hexane to obtain lamellar crystals.

mp: 88° C.

$^1$H-NMR (400 MHz, CDCl$_3$): δ4.36 (br s, 1H), 4.24 (br s, 1H), 3.69 (s, 3H), 2.10 (br s, 2H), 1.91-1.79 (m, 6H), 1.77-1.66 (m, 4H). $^{13}$C-NMR (100 MHz, CDCl$_3$): 6155.1, 52.2, 47.2, 46.7, 35.8, 35.7, 35.4, 26.7. IR (neat, cm$^{-1}$): 1,677. MS m/z: 195 (M$^+$), 195 (100%). HRMS (EI): Calcd. for C$_{11}$H$_{17}$NO 195.1259 (M$^+$). found: 195.1236.

Now, other methods for producing 2-azaadamantane will be described.

Preparation of N-trichloroacetyl-endo-bicyclo[3.3.1]non-6-en-3-ylamine

To a solution containing 15.6 g (0.11 mol) of endo-bicyclo[3.3.1]non-6-en-3-ylamine (3) and 46.8 g of toluene, 13.8 g (0.14 mol) of triethylamine was added, and after adjusting the temperature to 50° C., a solution containing 22.7 g (0.12 mol) of trichloroacetyl chloride and 31.2 g of toluene, was gradually dropwise added. Stirring was continued for one hour, and then, 31 g of water was added, followed by liquid separation to obtain a toluene solution of N-trichloroacetyl-endo-bicyclo[3.3.1]non-6-en-3-ylamine.

From the internal standard quantitative determination by GC, it was found that N-trichloroacetyl-endo-bicyclo[3.3.1]non-6-en-3-ylamine was contained in an amount of 31.2 g (0.11 mol). Yield: 97%.

$^1$H-NMR: 1.1-2.6 (m, 11H), 4.245 (br, m, 1H), 5.93 (m, 1H), 6.15 (m, 1H)

Preparation of N-trichloroacetyl-2-azaadamantane

A solution containing 31.2 g (0.11 mol) of N-trichloroacetyl-endo-bicyclo[3.3.1]non-6-en-3-ylamine and 93.5 g of toluene, was heated to 40° C., and 34.8 g (0.23 mol) of trifluoromethanesulfonic acid was gradually dropwise added. After stirring for one hour, 66 g of a 20 wt % NaOH aqueous solution was added, followed by liquid separation and further by washing with 31 g of water to obtain a toluene solution of N-trichloroacetyl-2-azaadamantane.

The internal standard quantitative determination was carried out by liquid chromatography, whereby it was found that N-trichloroacetyl-2-azaadamantane was contained in an amount of 23.4 g (0.083 mol). Yield: 75%.

$^1$H-NMR: 1.4-2.3 (m, 12H), 4.766 (br, m, 2H)

Preparation of 2-azaadamantane

A solution containing 23.4 g (83 mmol) of N-trichloroacetyl-2-azaadamantane and 70.1 g of isopropanol, was heated to 80° C., and 99.4 g of a 20 wt % NaOH aqueous solution was added, followed by stirring for one hour. 47 g of water and 47 g of toluene were added, followed by liquid separation, to obtain a toluene solution of 2-azaadamantane.

The internal standard quantitative determination was carried out by gas chromatography, whereby it was found that 2-azaadamantane was contained in an amount of 8.7 g (63 mmol). Yield: 77%.

Preparation of N-(2-nitrophenylsulfonyl)-endo-bicyclo[3.3.1]non-6-en-3-ylamine

To a solution containing 702 mg (5.10 mmol) of endo-bicyclo[3.3.1]non-6-en-3-ylamine (3) and 2.26 g of toluene, 0.68 g (6.72 mmol) of triethylamine was added, and after adjusting the temperature to 40° C., 1.29 g (5.83 mmol) of o-nitrobenzenesulfonyl chloride was gradually dropwise added. After stirring for 3 hours, the reaction solution was cooled to room temperature, and 1.43 g of water was added, followed by liquid separation and further by washing with 0.88 g of a saturated sodium hydrogen carbonate aqueous solution and 0.74 g of water, to obtain a toluene solution of N-(2-nitrophenylsulfonyl)-endo-bicyclo[3.3.1]non-6-en-3-ylamine.

The obtained toluene solution was concentration under reduced pressure to obtain N-(2-nitrophenylsulfonyl)-endo-bicyclo[3.3.1]non-6-en-3-ylamine (obtained amount: 1.77 g, yield: 107%).

$^1$H-NMR: 1.47-2.39 (m, 10H), 3.90 (m, 1H), 5.97 (m, 1H), 6.08 (m, 1H), 6.62 (m, 1H), 7.56-7.75 (m, 2H), 7.85-7.88 (m, 1H), 8.03-8.12 (m, 1H)

Preparation of N-(2-nitrophenylsulfonyl)-2-azaadamantane

To a solution containing 1.64 g (5.09 mmol) of N-(2-nitrophenylsulfonyl)-endo-bicyclo[3.3.1]non-6-en-3-ylamine and 9.83 g of toluene, 0.45 mL (5.09 mmol) of trifluoromethanesulfonic acid was gradually dropwise added at 20° C. After stirring for one hour, 5.01 g of water was added, followed by stirring, whereby a solid precipitated. 27.63 g of toluene was added to dissolve the solid, followed by liquid separation and further by washing with 4.99 g of a 5% sodium hydrogen carbonate aqueous solution and 9.83 g of water, to obtain a toluene solution of N-(2-nitrophenylsulfonyl)-2-azaadamantane.

The obtained toluene solution was concentrated under reduced pressure to obtain N-(2-nitrophenylsulfonyl)-2-azaadamantane (obtained amount: 1.57 g, yield: 95%).

H-NMR: 1.71-2.56 (m, 12H), 4.11 (br, 2H), 7.63-7.67 (m, 3H), 7.98-8.09 (m, 1H)

Preparation of 2-azaadamantane

To 100 mg (0.311 mmol) of N-(2-nitrophenylsulfonyl)-2-azaadamantane, 51.6 mg (0.373 mmol) of potassium carbonate and 0.54 g of toluene were added, and after adjusting the temperature to 50° C., 0.039 mL (0.380 mmol) of thiophenol was added. After stirring for 5 hours, acetonitrile, methanol and water were added to obtain a uniform solution of 2-azaadamantane.

The absolute quantitative determination was carried out by LC-MS, whereby it was found that 2-azaadamantane was contained in an amount of 37.71 mg (0.275 mmol). Yield: 88%.

INDUSTRIAL APPLICABILITY

According to the present invention, it is possible to efficiently produce 2-azaadamantane and a 2-azaadamantane having a substituent, which are useful as intermediates for a 2-azaadamantane-N-oxyl (AZADO) compound useful as a catalyst for oxidation of an alcohol, and thus, the production method of the present invention is very useful.

The entire disclosure of Japanese Patent Application No. 2007-300919 filed on Nov. 20, 2007 including specification, claims, drawings and summary is incorporated herein by reference in its entirety.

The invention claimed is:

1. A method for producing a 2-azaadamantane formula (1):

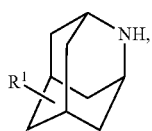

(1)

the method comprising cyclizing, in the presence of an acid, a compound of formula (2):

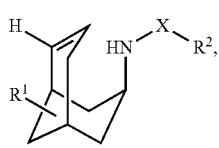

(2)

wherein:
the cyclizing of the compound of formula (2) forms a compound of formula (3), such that the cyclizing directly forms a N—C bond at a first position and a C—H bond at a second position adjacent to the first position, as follows:

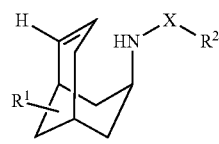

(2)

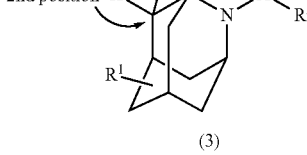

(3)

—X—$R^2$ is —C(=O)—$R^2$, —C(=O)—O—$R^2$ or —$SO_2$—$R^2$;

$R^2$ is a hydrogen atom, a $C_{1-12}$ alkyl group optionally substituted by $R^a$, a $C_{1-12}$ cycloalkyl group optionally substituted by $R^a$, a $C_{2-12}$ haloalkyl group, a benzyl group optionally substituted by $R^a$, or an aryl group optionally substituted by $R^a$;

$R^1$ is at least one substituent selected from the group consisting of a hydrogen atom, a halogen atom, a nitro group, a cyano group, a hydroxy group, a mercapto group, an amino group, a formyl group, a carboxyl group, a sulfo group, a $C_{1-12}$ alkyl group, a $C_{3-12}$ cycloalkyl group, a ($C_{1-12}$ alkyl)oxy group, a ($C_{3-12}$ cycloalkyl)oxy group, a ($C_{1-12}$ alkyl)thio group, a ($C_{3-12}$ cycloalkyl)thio group, a ($C_{1-12}$ alkyl)amino group, a ($C_{3-12}$ cycloalkyl)amino group, a di($C_{1-6}$ alkyl)amino group, a di($C_{3-6}$ cycloalkyl)amino group, a ($C_{1-12}$ alkyl)carbonyl group, a $C_{3-12}$ cycloalkylcarbonyl group, a ($C_{1-12}$ alkyl)oxycarbonyl group, a ($C_{3-12}$ cycloalkyl)oxycarbonyl group, a ($C_{1-12}$ alkyl)thiocarbonyl group, a ($C_{3-12}$ cycloalkyl)thiocarbonyl group, a ($C_{1-12}$ alkyl)aminocarbonyl group, a ($C_{3-12}$ cycloalkyl)aminocarbonyl group, a di($C_{1-6}$ alkyl)aminocarbonyl group, a di($C_{3-6}$ cycloalkyl)aminocarbonyl group, a ($C_{1-12}$ alkyl)carbonyloxy group, a ($C_{3-12}$ cycloalkyl)carbonyloxy group, a ($C_{1-12}$ alkyl)carbonylthio group, a ($C_{3-12}$ cycloalkyl)carbonylthio group, a ($C_{1-12}$ alkyl)carbonylamino group, a ($C_{3-12}$ cycloalkyl)carbonylamino group, a di{($C_{1-12}$ alkyl)carbonyl}amino group, a di{($C_{3-12}$ cycloalkyl)carbonyl}amino group, a $C_{1-6}$ haloalkyl group, a $C_{3-6}$ halocycloalkyl group, a $C_{2-6}$ alkenyl group, a $C_{3-6}$ cycloalkenyl group, a $C_{2-6}$ haloalkenyl group, a $C_{3-6}$ halocycloalkenyl group, a $C_{2-6}$ alkynyl group, a $C_{2-6}$ haloalkynyl group, a benzyl group optionally substituted by $R^a$, a benzyloxy group optionally substituted by $R^a$, a benzylthio group optionally substituted by $R^a$, a benzylamino group optionally substituted by $R^a$, a dibenzylamino group optionally substituted by $R^a$, a benzylcarbonyl group optionally substituted by $R^a$, a benzyloxycarbonyl group optionally substituted by $R^a$, a benzylthiocarbonyl group optionally substituted by $R^a$, a benzylaminocarbonyl group optionally substituted by $R^a$, a dibenzylaminocarbonyl group optionally substituted by $R^a$, a benzylcarbonyloxy group optionally substituted by $R^a$, a benzylcarbonylthio group optionally substituted by $R^a$, a benzylcarbonylamino group optionally substituted by $R^a$, a di(benzylcarbonyl)amino group optionally substituted by $R^a$, an aryl group optionally substituted by $R^a$, an aryloxy group optionally substituted by $R^a$, an arylthio group optionally substituted by $R^a$, an arylamino group optionally substituted by $R^a$, a diarylamino group optionally substituted by $R^a$, an arylcarbonyl group optionally substituted by $R^a$, an aryloxycarbonyl group optionally substituted by $R^a$, an arylthiocarbonyl group optionally substituted by $R^a$, an arylaminocarbonyl group optionally substituted by $R^a$, a diarylaminocarbonyl group optionally substituted by $R^a$, an arylcarbonyloxy group optionally substituted by $R^a$, an arylcarbonylthio group optionally substituted by $R^a$, an arylcarbonylamino group optionally substituted by $R^a$, and a di(arylcarbonyl)amino group optionally substituted by $R^a$, and when the number of substituents is two or more, the respective substituents are optionally the same or different; and $R^a$ is from 1 to 5 substituents selected from the group consisting of a halogen atom, a $C_{1-6}$ alkyl group, a $C_{1-6}$ haloalkyl group, a $C_{3-6}$ cycloalkyl group, a ($C_{1-6}$ alkyl)oxy group, a ($C_{1-6}$ alkyl)oxy ($C_{1-6}$ alkyl) group, a ($C_{1-6}$ alkyl)sulfenyl ($C_{1-6}$ alkyl) group, a $C_{1-6}$ haloalkoxy group, a ($C_{1-6}$ alkyl)sulfenyl group, a ($C_{1-6}$ alkyl)sulfinyl group, a ($C_{1-6}$ alkyl)sulfonyl group, a ($C_{1-6}$ haloalkyl)sulfenyl group, a ($C_{1-6}$ haloalkyl)sulfinyl group, a ($C_{1-6}$ haloalkyl)sulfonyl group, a $C_{2-6}$ alkenyl group, a $C_{2-6}$ haloalkenyl group, a ($C_{2-6}$ alkenyl)oxy group, a ($C_{2-6}$ haloalkenyl)oxy group, a ($C_{2-6}$ alkenyl)sulfenyl group, a ($C_{2-6}$ alkenyl)sulfinyl group, a ($C_{2-6}$ alkenyl)sulfonyl group, a ($C_{2-6}$ haloalkenyl)sulfenyl group, a ($C_{2-6}$ haloalkenyl)sulfinyl group, a ($C_{2-6}$ haloalkenyl)sulfonyl group, a $C_{2-6}$ alkynyl group, a $C_{2-6}$ haloalkynyl group, a ($C_{2-6}$ alkynyl)oxy group, a ($C_{2-6}$ haloalkynyl)oxy group, a ($C_{2-6}$ alkynyl)sulfenyl group, a ($C_{2-6}$ haloalkynyl)sulfinyl group, a ($C_{2-6}$ alkynyl)sulfonyl group, a ($C_{2-6}$ haloalkynyl)phenyl group, a ($C_{2-6}$ haloalkynyl)sulfinyl group, a ($C_{2-6}$ haloalkynyl)sulfonyl group, $NO_2$, CN, a formyl group, OH, SH, $NH_2$, SCN, a ($C_{1-6}$ alkyl)oxycarbonyl group, a ($C_{1-6}$ alkyl)carbonyl group, a ($C_{1-6}$ haloalkyl)carbonyl group, a ($C_{1-6}$ alkyl)carbonyloxy group, a phenyl group, a ($C_{1-6}$ alkyl)amino group and a di($C_{1-6}$ alkyl)amino group, and when the number of substituents is two or more, the respective substituents are optionally the same or different.

2. The method of claim 1, wherein the acid is trifluoromethanesulfonic acid.

3. The method of claim 1, wherein $R^1$ in the formulae (1), (2) and (3) is a hydrogen atom.

4. The method of claim 1, wherein:
—X—$R^2$ is —C(=O)—O—$R^2$; and
$R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group optionally substituted by $R^a$, or an aryl group optionally substituted by $R^a$.

5. The method of claim 1, wherein:
—X—$R^2$ is —C(=O)—$R^2$; and
$R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group optionally substituted by $R^a$, or an aryl group optionally substituted by $R^a$.

6. The method of claim 1, wherein:
—X—$R^2$ is —$SO_2$—$R^2$; and
$R^2$ is a $C_{2-12}$ alkyl group, a $C_{1-12}$ monohaloalkyl group, a $C_{1-12}$ dihaloalkyl group, a benzyl group optionally substituted by $R^a$, or an aryl group optionally substituted by $R^a$.

7. The method of claim 2, wherein $R^1$ in the formulae (1), (2) and (3) is a hydrogen atom.

8. The method of claim 2, wherein:
—X—$R^2$ is —C(=O)—O—$R^2$; and
$R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group optionally substituted by $R^a$, or an aryl group optionally substituted by $R^a$.

9. The method of claim 3, wherein:
—X—$R^2$ is —C(=O)—O—$R^2$; and
$R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group optionally substituted by $R^a$, or an aryl group optionally substituted by $R^a$.

10. The method of claim 2, wherein:
—X—$R^2$ is —C(=O)—$R^2$; and
$R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group optionally substituted by $R^a$, or an aryl group optionally substituted by $R^a$.

11. The method of claim 3, wherein:
—X—$R^2$ is —C(=O)—$R^2$; and
$R^2$ is a $C_{2-12}$ alkyl group, a $C_{3-12}$ cycloalkyl group, a $C_{1-12}$ monohaloalkyl group, a $C_{1-12}$ dihaloalkyl group, a benzyl group optionally substituted by $R^a$, or an aryl group optionally substituted by $R^a$.

12. The method of claim 2, wherein:
—X—$R^2$ is —$SO_2$—$R^2$; and
$R^2$ is a $C_{2-12}$ alkyl group, a $C_{1-12}$ monohaloalkyl group, a $C_{1-12}$ dihaloalkyl group, a benzyl group optionally substituted by $R^a$, or an aryl group optionally substituted by $R^a$.

13. The method of claim 3, wherein:
—X—$R^2$ is —$SO_2$—$R^2$; and
$R^2$ is a $C_{2-12}$ alkyl group, a $C_{1-12}$ monohaloalkyl group, a $C_{1-12}$ dihaloalkyl group, a benzyl group optionally substituted by $R^a$, or an aryl group optionally substituted by $R^a$.

* * * * *